United States Patent
Bakalyar

[19]

[11] Patent Number: 6,155,123
[45] Date of Patent: Dec. 5, 2000

[54] MULTIVALVING SAMPLE INJECTION SYSTEM

[75] Inventor: Steve Bakalyar, Sebastopol, Calif.

[73] Assignee: Rheodyne, L.P., Rohnert Park, Calif.

[21] Appl. No.: 09/062,414

[22] Filed: Apr. 17, 1998

[51] Int. Cl.[7] ................................................ G01N 30/20
[52] U.S. Cl. ................ 73/864.83; 73/61.55; 73/864.22; 73/864.84; 73/864.87
[58] Field of Search ............................... 73/61.55, 61.56, 73/863.72, 863.73, 864.21, 864.22, 864.25, 864.81, 864.83–864.87

[56] References Cited

U.S. PATENT DOCUMENTS

| | | | |
|---|---|---|---|
| 4,158,630 | 6/1979 | Stearn | 73/61.55 X |
| 4,242,909 | 1/1981 | Gundelfinger . | |
| 4,506,558 | 3/1985 | Bakalyar | 73/863.72 |
| 4,625,569 | 12/1986 | Toei et al. | 73/864.83 |
| 5,650,577 | 7/1997 | Nagai et al. | 73/864.83 X |

FOREIGN PATENT DOCUMENTS

| | | | |
|---|---|---|---|
| 175355 | 7/1991 | Japan | 73/61.55 |

Primary Examiner—Thomas P. Noland
Attorney, Agent, or Firm—Leon D. Rosen

[57] ABSTRACT

A sample inject valve system is described, which enables a modified sample injection valve to perform many functions that are required to inject a sample into a chromatographic column, to minimize the amount of laboratory table space previously occupied by equipment and to organize and minimize the number of tubular fluid connections. The modified valve includes a stator (70) with twelve passages (1–12) lying on a circle (74) centered on a rotor axis (76) and a rotor (72) with four channels (A, B, C, D) for connecting selected passages. The stator passages are spaced 30° apart to lie at the twelve positions of a clock face. Each rotor channel has channel ends spaced by 30° and with the ends of different but adjacent channels spaced apart by 60°. Not only are the usual column (17), pump (44), sample loop ends, and metering syringe (42) connected to stator passages, but a rinse syringe (52), rinse reservoir (60), waste syringe (62), and rinse nozzle (56) are connected to other stator passages. The rotor has a radially-extending channel part (90) with its outer end lying halfway between first and second channels (A, B) and with its inner end lying at the rotor axis and connected to a stator passage part (100) that extends along the axis, to couple the pump to a third passage at all rotor positions.

3 Claims, 5 Drawing Sheets

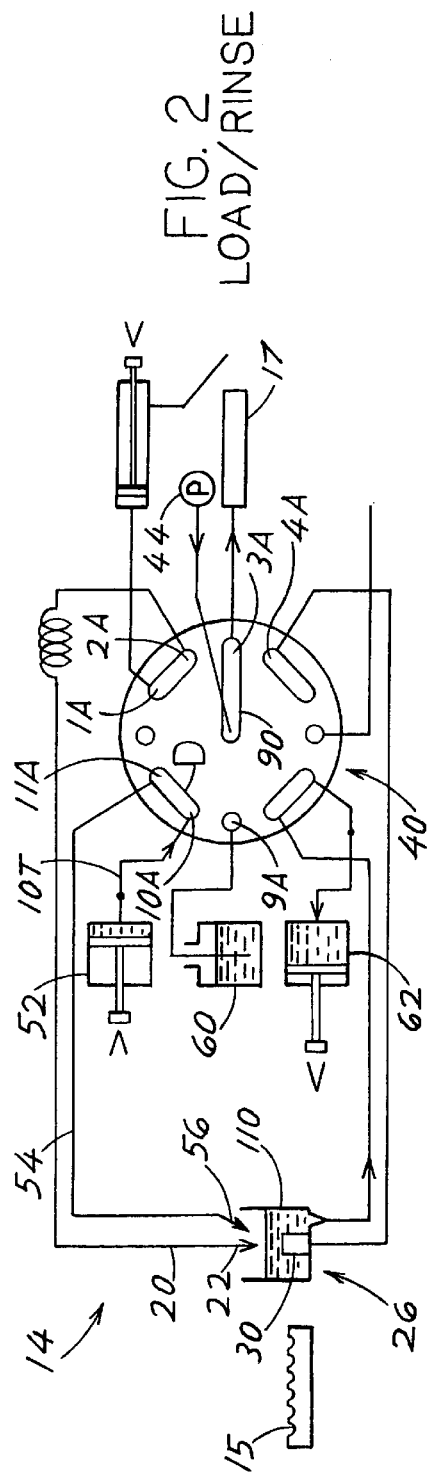
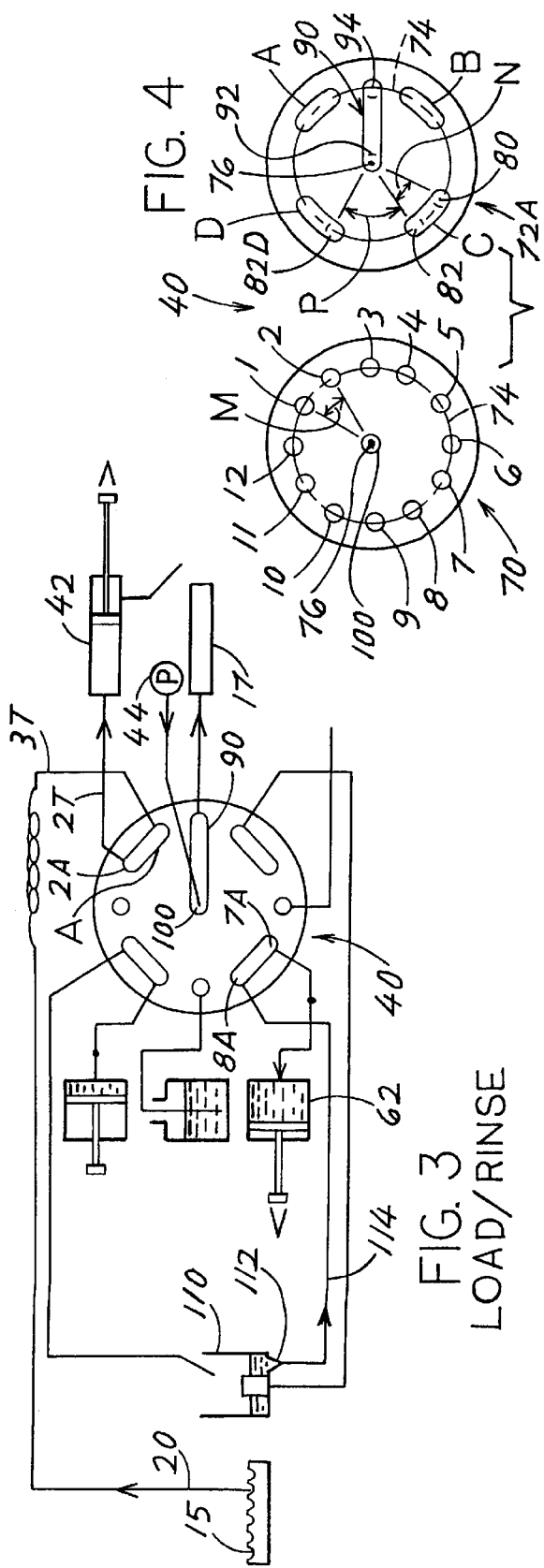

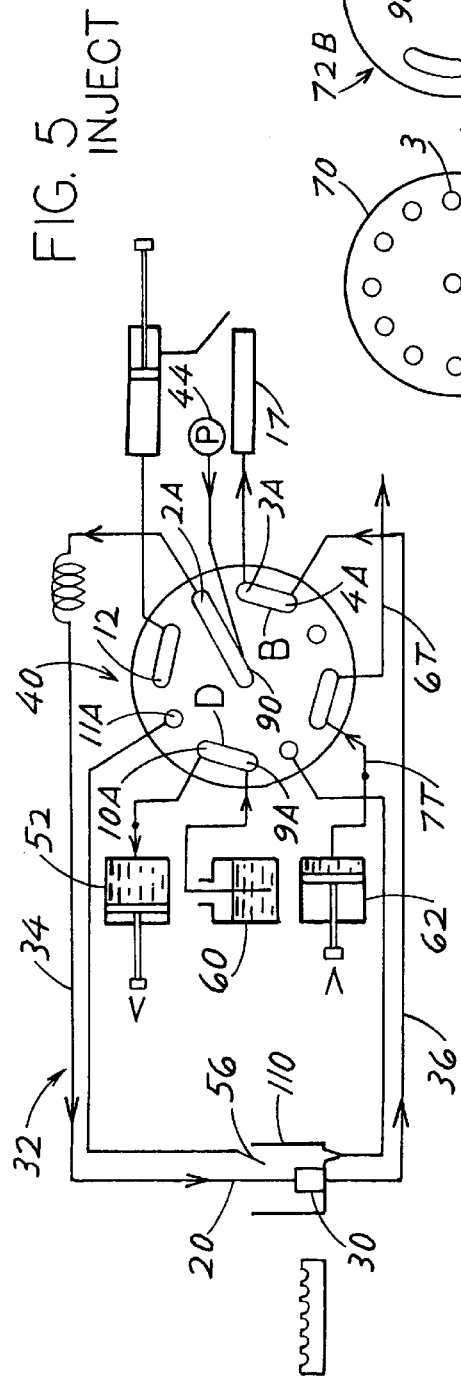
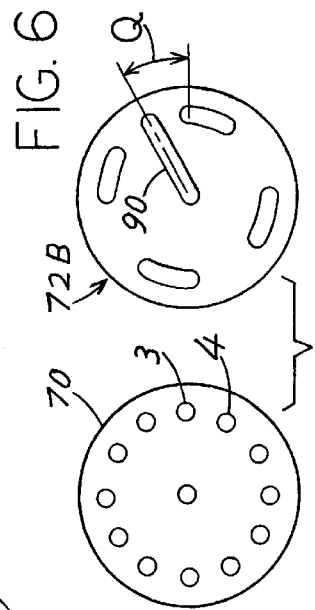
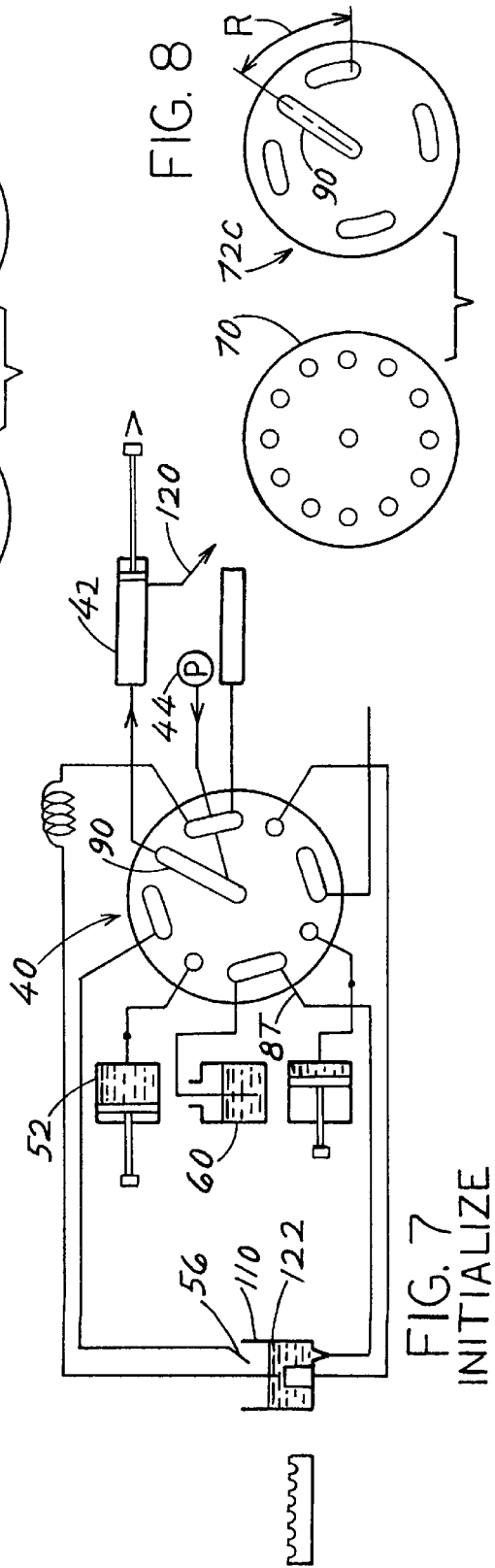

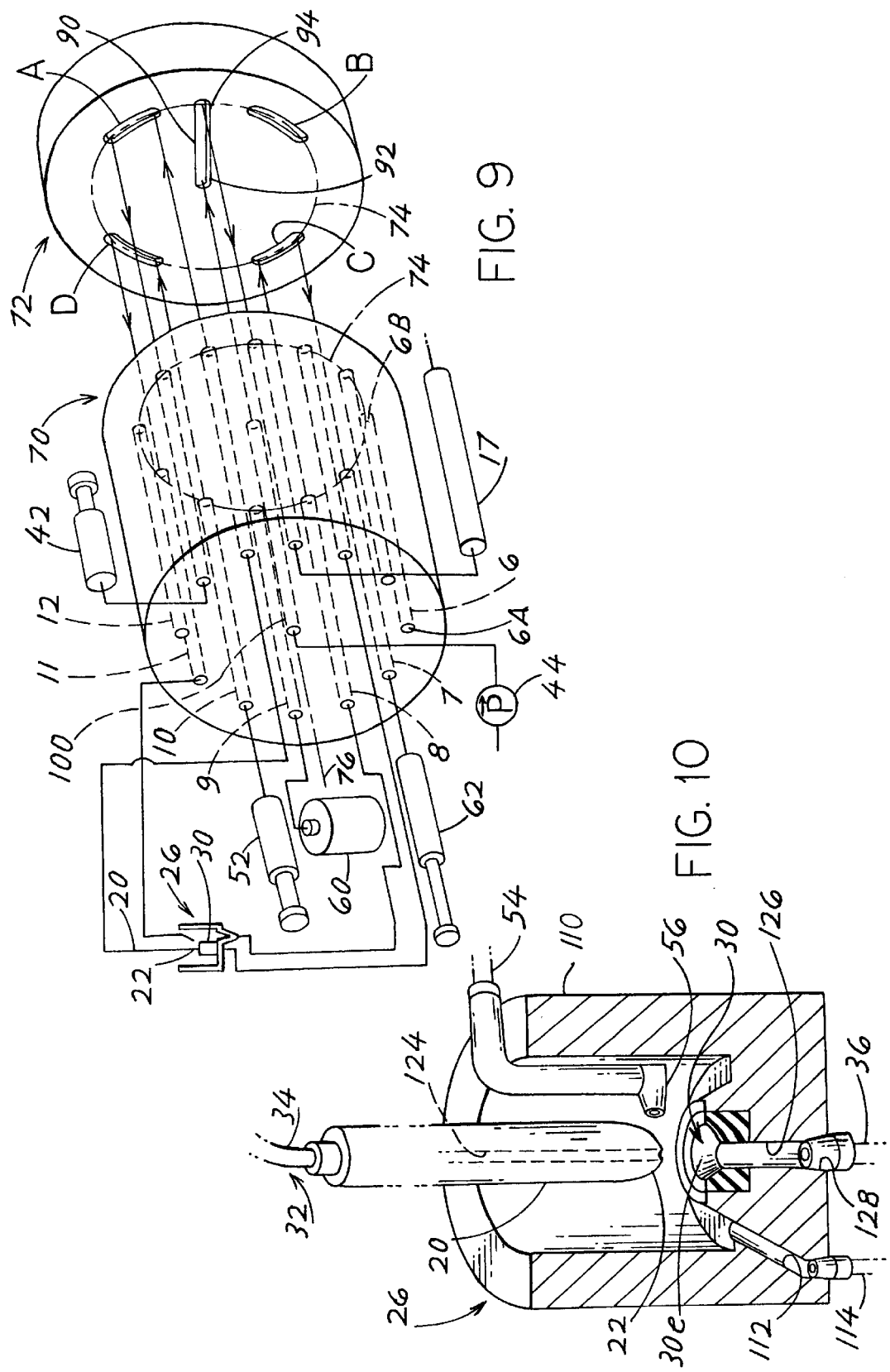

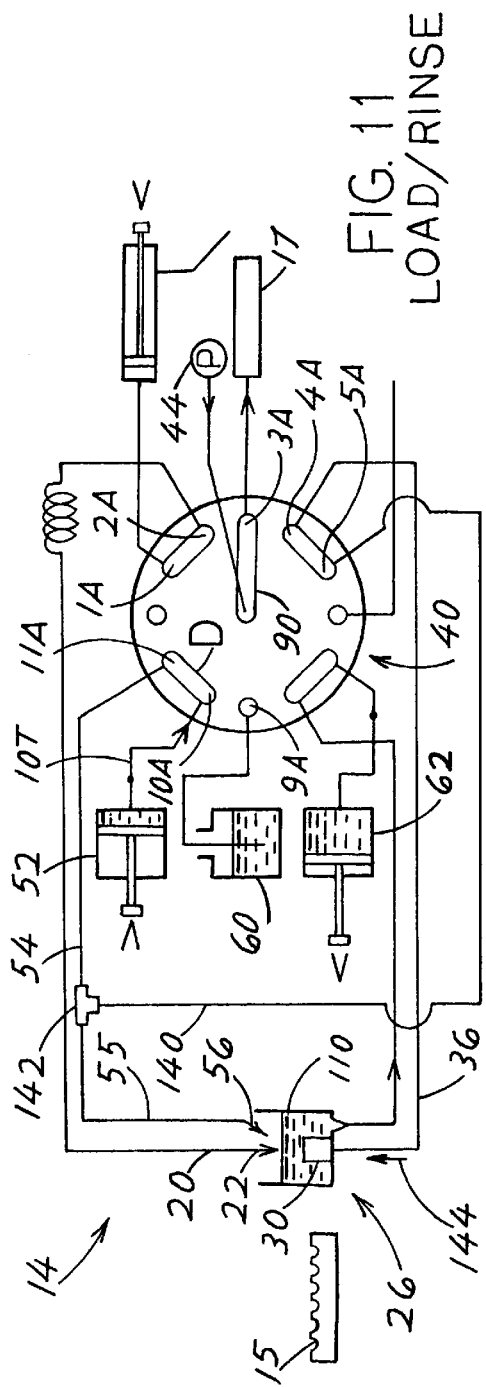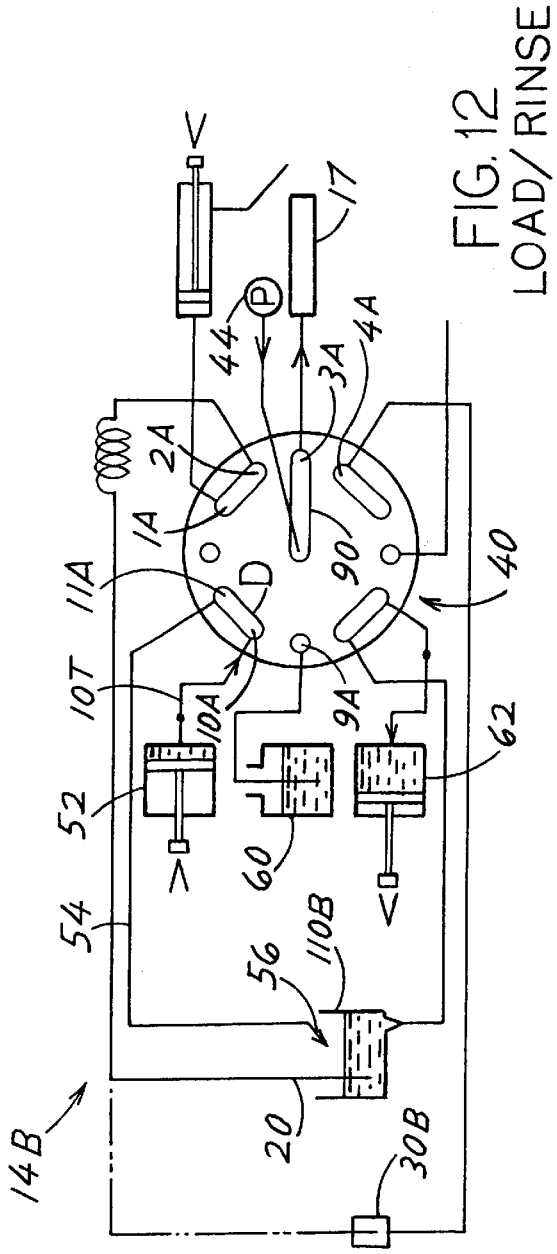
FIG. 11 LOAD/RINSE
FIG. 12 LOAD/RINSE

MULTIVALVING SAMPLE INJECTION SYSTEM

BACKGROUND OF THE INVENTION

A large number of samples can be injected at high pressure into a chromatographic column in a system that uses an injector valve. At the start of a cycle, the tip of a probe is moved into a sample well to withdraw a sample, and then to a wash station to wash the probe tip. The probe tip then moves against a dock and high pressure mobile phase fluid moves from a pump through the valve and through a sample loop that includes the probe and dock in series, and again through the valve to the column. Prior to loading the probe with a sample, the valve connects the pump to the column to continually pass mobile phase fluid through the column. To draw a sample into the probe, a metering syringe is connected through the valve to the probe. For probe washing, a rinse syringe is connected to a rinse nozzle to supply pressured fluid thereto, while occasionally fluid from a reservoir reloads the rinse syringe. In addition, rinsing fluid sprayed by the nozzle into a cup to wash the probe tip, is drained to a waste syringe. Furthermore, the metering syringe is connected directly to the mobile phase pump, as required (typically at the start of the days work) so as to remove gas bubbles. It can be appreciated that in such a system a large number of items are used, and there are a large number of tubes and means for interconnecting the tubes at different times in the cycle.

A prior injection valve performs many of the functions required, but with the addition of a cleaning nozzle and associated equipment additional switching of flow is required. It would be possible to add another valve similar to a prior injection valve to perform switching for the rinsing functions, but this would add cost and size, and reduce reliability. Modern laboratories have limited bench space, and they demand extremely high system reliability, even while placing a high premium on economy. A single valve that could automatically connect the proper tubes at the proper times in the cycle would reduce cost and size, and would increase reliability. However, present injection valves such as shown in U.S. Pat. No. 4,242,909 include a single circle of holes and a single rotor with channels that connect pairs of holes. Pivoting of the channel to a different position connects all channels to different pairs of holes. It is difficult to construct such a valve to perform all functions of injection and cleaning so the proper connections are made at every time during a sampling cycle.

SUMMARY OF THE INVENTION

In accordance with one embodiment of the present invention, a sample injector valve system is provided that enables the switching of numerous connections required not only in sample injection, but in probe cleaning and metering syringe flushing. The system includes sample-control apparatus including a pump for supplying high pressure mobile phase fluid, a chromatographic column or other analyzing device, a sample metering syringe for withdrawing a predetermined sample volume into a probe, and a sample loop that includes the probe and a dock. The system also includes probe washing apparatus that includes a rinse syringe for supplying pressured wash fluid to a nozzle, a rinse reservoir for refilling the rinse syringe, and a waste syringe for withdrawing rinsing fluid from a cup into which the nozzle has deposited rinse fluid. The system also includes a sample syringe connection to the valve for flushing gas bubbles from the syringe. A valve of the type that includes a stator with a circle of passages and a rotor that has channels that can connect different pairs of passages as the rotor pivots to different positions, is provided to make the connections.

The valve connects to the usual sample-control apparatus including opposite ends of the sample loop, a metering syringe, a chromatographic column, and a pump. However, the valve also connects to probe rinsing apparatus including a probe-cleaning nozzle, a rinse syringe, a rinse reservoir, and a waste syringe, that otherwise would require several valves for proper interconnection at different times in the sampling cycle, or require a separate valve similar to the prior art valve. By combining the sample control and probe rinsing functions, and syringe flushing functions in a single valve that properly switches its different passages, applicant reduces the size and cost of the system, and increases system reliability.

The valve includes a stator with at least nine (and preferably twelve) passages spaced 30° apart about a circle concentric with the rotor axis of rotation. The rotor has four channels with channel ends lying on the same circle. The opposite ends of each channel are spaced 30° apart while the ends of different channels are spaced apart by 60°. In addition, the stator has a pump port part that extends through the stator near its axis, and the rotor has a channel part that continually connects the pump port part to a rotor location lying between two channels.

A combination dock and wash station is provided, where the probe can be connected to the dock to connect all parts of the sample loop in series for sample injection. The combination dock and wash station also includes a washing capability for cleaning the probe tip after a sample is injected into the column or before it is connected to the dock. The washing station can include a nozzle for emptying cleaning fluid into the cup and possibly with the probe directing the cleaning fluid directly at the probe tip.

The novel features of the invention are set forth with particularity in the appended claims. The invention will be best understood from the following description when read in conjunction with the accompanying drawings.

BRIEF DESCRIPTION OF THE DRAWINGS

FIG. 2 is a schematic diagram of the system of FIG. 1, showing the injection valve thereof in a load/rinse position and being used to rinse the probe.

FIG. 3 is a view similar to that of FIG. 2, with the valve in the load/rinse position, and being used to load the probe with a sample.

FIG. 4 is an exploded front elevation view of the stator and rotor of the injection valve of FIGS. 1–3 in the load/rinse position.

FIG. 5 is a view similar to that of FIG. 2, but with the rotor having been turned so the valve is in an inject position.

FIG. 6 is an exploded view similar to that of FIG. 4, but with the rotor having been turned so the valve is in the inject position.

FIG. 7 is a view similar to that of FIG. 5, but with the rotor having been turned further so the valve is in an initialized position.

FIG. 8 is an exploded view similar to that of FIG. 4, but with the valve in the initialized position.

FIG. 9 is a simplified isometric exploded view of the injector valve of FIGS. 1–8, with the valve in the load/rinse position.

FIG. 10 is a sectional isometric view showing the combination dock and wash station of FIG. 1.

FIG. 11 is a schematic diagram of a system of another embodiment of the invention, in a load/rinse position.

FIG. 12 is a schematic diagram of a system of another embodiment of the invention, in a load/rinse position.

DESCRIPTION OF THE PREFERRED EMBODIMENTS

Figure 1:
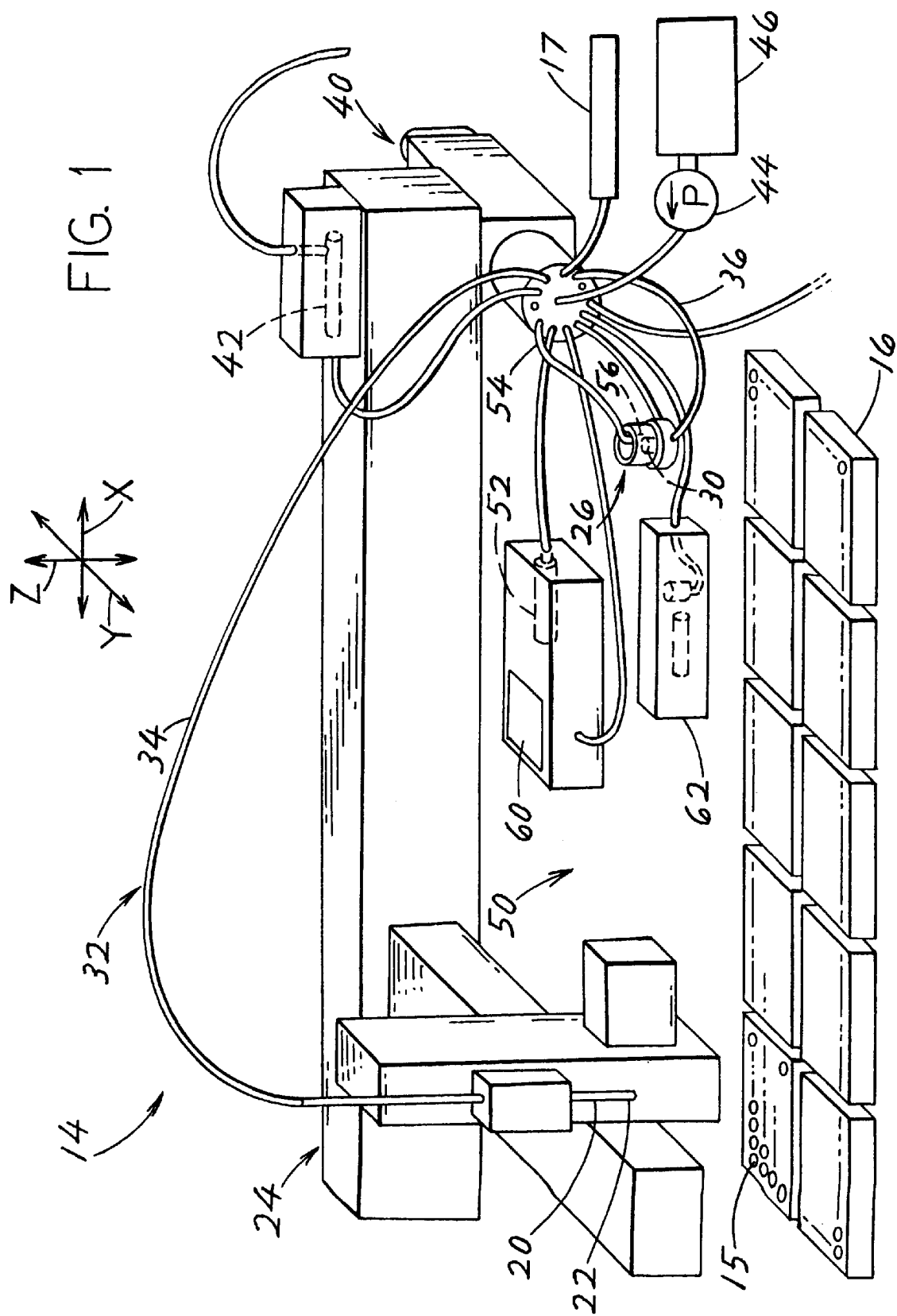
FIG. 1 is an isometric view showing a sample injector valving system of the present invention.

FIG. 1 illustrates a sample injector valving system 14. The system is designed to take samples from containers or wells 15 of microplates 16 and inject the samples through a chromatographic column 17 or other analyzing instrument. In one example, each microplate 16 has 96 or 184 wells, and there are many microplates. A sample from each well is drawn by a probe 20 whose tip 22 is moved down into a well, with a metered amount of sample then drawn into the probe. A three-axis precision positioner at 24 moves the probe up out of the well and to a combination dock and rinse station 26. At the station 26, the probe 20 is moved down to press the probe tip against a dock 30 to seal thereagainst. The sample is then moved along a sample loop 32 that includes the probe and dock, by pumping mobile phase fluid (e.g. a mixture of water and acetonitrile) through a first sample loop part, through the probe 20 and dock 30, and through a second sample loop part 36 to an injector valve 40. The sample then moves through the valve to the column 17.

Several instruments are required to effect the sample injection. A motorized metering syringe 42 is connected through the valve 40 to the first sample loop part 34 to apply a vacuum to the probe 20 to draw in a predetermined volume of sample. A pump 44 pumps high pressure mobile phase fluid (e.g. at thousands of psi) from a supply 46 to the valve to flow fluid into the first sample loop part 34 and through the docked probe, the dock, and the lower sample loop part 36 and then into the column 17. When a sample is being taken, the output of the pump 44 is connected to the column 17 to keep the column continually filled with flowing mobile phase fluid.

Additional instruments include a set 50 of rinsing instruments or devices for washing or rinsing the probe after its tip dips into a well and the sample is injected, to prevent cross-contamination of samples. The set includes a motorized flushing syringe 52 that delivers pressured rinsing fluid through the valve 40 to a rinse tube 54 that leads to a rinse nozzle 56. In the particular apparatus illustrated in FIGS. 1–10, the rinse nozzle directs rinsing fluid directly at the tip 22, but only when the tip lies within the combination station 26. A rinse reservoir 60 refills the flushing syringe 52 after (but not during) one or several cleanings of the probe. A drain syringe 62 takes away rinsing solution that has been deposited in the combination station 26 after each rinsing. It can be appreciated that all of the functions of the different devices must be performed in a selected sequence during a sampling cycle.

Presently, the functions of taking and injecting a sample are performed by an injector valve by turning the rotor between load and inject positions. However, the operation of the set of rinse devices 50 is presently performed separately to switch valves and to control motors. The existence of additional switching valves adds to the size and cost of prior systems, and reduces reliability. The present system shown in FIG. 1 allows a single motorized valve to interconnect and control fluid flow throughout the system components, in order to perform the functions of injecting sample, rinsing the probe, and flushing the metering syringe. A single valve is not only more compact and simpler, but reduces the number of seals that can leak.

FIG. 4 is a simplified view of the injection valve 40 which includes a stator 70 and a rotor 72 (shown at load/rinse position 72A). The stator has twelve passages labeled 1–12 that lie on an imaginary circle 74 whose center is coincident with an axis of rotation 76 of the rotor with respect to the stator. It is noted that the twelve positions 1–12 of the stator passages correspond to the positions of numbers on a clock face, in that the angle M between the centers of adjacent passages is 30°. The rotor 72 has four channels A, B, C, and D. Each channel has opposite ends 80, 82 that lie on the imaginary circle 74 (as viewed along the axis 76). The angle N between the centers of each channel ends is 30°, so each channel can connect to adjacent passages of the stator. The ends 82, 82D of adjacent channels are angularly spaced by an angle P of 60°, which equals twice the spacing M of adjacent passages. It is also noted that the rotor has a pump channel part 90 with one end 92 at the axis and an opposite end 94 lying halfway between two channels A and B. Also, the stator 70 has a pump passage part 100 that lies along the axis 76 to always be connected to the end 92 of the pump channel part 90.

FIG. 9 shows some details of the stator and rotor 70, 72, including the stator passages 1–12 and the rotor channels A–D. Each passage 1–12 has opposite ends, with one end such as 6A being referred to herein as the port of that passage, with most of such ports being connected to a tube that extends to a device outside the valve. The other end of each passage such as 6B is referred to herein as a passage end, with each passage end being connected to an end of one of the rotor channels A–D. It is noted that in the system of FIGS. 1–10, the stator passages 5 and 12 are not used and can be eliminated if desired.

FIG. 3 shows the sample injector valving system 14 load/rinse position, with the probe 20 having been moved to a well 15. At this time the metering syringe 42 is operated to apply a vacuum through tube 2T to the second port 2A and through the first rotor channel A, to apply the vacuum through a tube 3T. The tube 3T applies the vacuum to the probe to draw in a sample. The probe 20 is then moved to the position shown in FIG. 2.

FIG. 2 shows the valve 40 in the same load/rinse as FIG. 3. However, the probe tip 22 now lies within a rinse cup 110 of the combination dock/wash station 26, and the system is being operated to rinse the probe tip. The motorized flushing syringe 52 is operated to pump fluid through a tube 10T that connects to the stator port 10A. Fluid passes through the rotor channel D to the stator port 11A and passes through rinse tube 54 to the rinse nozzle 56 to wash off any sample liquid lying on the probe tip. By cleaning the probe tip prior to injection, any sample clinging to the outside of the probe tip is washed away.

In the load/rinse position of both FIGS. 2 and 3, the output from the pump 44 continues to be directed through the pump passage part 90 to the column 17. Also, in FIGS. 2 and 3 a cup outlet 112 is connected through a drain tube 114 to port 8A, and from port 7A to the waste syringe 62 to draw out rinse fluid from the cup 110.

FIG. 5 shows the valve 40 in an inject position, with FIG. 6 showing details of the rotor in the inject position. The rotor at 72B has been rotated counterclockwise by an angle Q of 30° from the position of FIG. 4. In FIG. 5, the probe 20 has already been connected to the dock 30 so the probe, dock, and sample loop parts 34,36 are connected in series. In FIGS. 5 and 6 the channel part 90 connects the pump 44 through the channel part 90 and through the port 2A to flow mobile phase fluid and the sample through the loop 32 to the fourth port 4A. Fluid moves through the fourth port 4A and channel B to the third port 3A to flow to the column 17.

It is noted that the fourth channel D has moved out of connection with the eleventh port 11A that connects to the nozzle 56. Instead, the channel D connects the ninth and tenth ports 9A and 10A. When the valve is in the position of FIG. 5, the motorized syringe 52 can be returned towards its initial filled position. During such movement, rinse fluid from the rinse reservoir 60 is drawn out of the rinse reservoir and through the channel D to the rinse syringe 52 to refill it. In this position of the rotor, the motorized waste or drain syringe can be operated to pump out fluid therein that it previously received from the cup 110, to dispose of the rinse fluid through a waste tube 6T that leads to a dump such as a sink basin.

FIGS. 7 and 8 show the system in an initialize position, when the valve rotor at 72C has been turned counterclockwise by an angle R of 60° from the load/rinse position, and 30° from the position of FIG. 6. In the initialized position, which may occur only at the beginning of each day, the channel part 90 connects the pump 44 to the metering syringe device 42 to pump mobile phase fluid a through it to clean it of "stale" mobile phase fluid which is vented through an outlet 120 and refill it with fresh fluid. A significant advantage of applicant's system is that the metering syringe is not in line with the sample loop during injection, and thus does not add a delay volume between the pump and the column. At the beginning of the day, the rotor can be turned to the other positions, of FIGS. 2 and 5, to perform other functions including passing fresh rinse fluid through the nozzle 56, draining the cup 110, and filling the rinse syringe 52.

It is noted that the rotor position of FIG. 6 may be considered to be a "center" position, with the positions of FIGS. 4 and 6 being "extreme" positions lying on opposite sides (respectively angled 30° counterclockwise and 30° clockwise) from the center position.

FIG. 10 shows some details of the combination dock and rinse station 26. When the probe has just drawn a sample from a well, the positioner moves the probe over the cup 110 and lowers the probe until the probe tip 22 lies a distance of perhaps a few millimeters above the dock. The probe tip is then rinsed. Then the probe is lowered until the probe tip presses against a probe-coupling end (30e) of the dock 30. As described above, pressured mobile phase fluid is then pumped through the loop 32, including probe and dock passages 124, 126. The fluid moves from a distal end 128 of the dock passage, which is opposite the probe-coupling end 30e, and through the sample loop part 36 so the sample is pumped through the column. Previously, the probe was lowered into a cup filled with rinse fluid, lifted out of the cup, and then moved over and down against the dock. Applicant combines the dock and the rinse cup into a single station, so a separate dock and cup do not have to be precisely positioned and the probe does not have to be separately moved down into each.

The last passage 12 (not counting passage part 100) is not necessary, although it can be used to vent the metering syringe 42 in the position of FIG. 5. The fifth passage 5 is optional. If present, it allows the sample loop to be depressurized when the valve is returned to the position of FIG. 2. This is useful if it is desireable to avoid pressurizing the metering syringe 42. The nine passages 1–4 and 7–11 are necessary for the valve to operate in the manner described above. The stator is preferably constructed so opposite ends of each passage, such as port 6A and passage end 6B (FIG. 9), lie on the imaginary circle 74 as viewed along axis 76. However, it is only necessary that the passage ends that connect to the channels, lie on the same circle as the channels.

It would be possible to have two sets of passage and channels lying on two concentric circles of different diameters, one set for the sample-control apparatus and the other set for the rinse apparatus. Pivoting of a single rotor then would switch all equipment. However, this has some disadvantage in that it would require an additional seal between the two circles at the stator-rotor interface. It would be possible to rotate the stator while the rotor remains stationary instead of vice versa, although this is the equivalent of the arrangement illustrated.

FIG. 11 illustrates a modified system 14A similar to that of FIG. 2, except that a different connection is made to the combination dock and rinse station 26. A line 140 extends from a T-connection 142 in line 54, to port 5A. As a result, when rinsing fluid passes from the flushing syringe 52 and lines 54, 55 to the nozzle 56 to clean a probe tip, some of the rinsing fluid also passes through line 140. Rinsing fluid passes along line 140 through valve ports 5A and 4A and through the lower sample loop part 36 to dock 30. This fluid moving along arrow 144 to the dock, washes away any sample on the dock seat to decontaminate it. The T-connection and/or lines (possibly with adjustable chokes) are preferably made so more of the rinsing fluid (e.g. 90%) passes to the nozzle 56, than along arrow 144 to the dock (e.g. 10%).

FIG. 12 illustrates another modified system 14B, where the rinse cup 110B is separate from the dock 30B. The probe 20 is shown in solid lines, immersed in the rinsing liquid in the cup, and is shown in phantom lines engaged with the dock.

Thus, the invention provides a system that enables not only sample control (loading and injecting) equipment to be connected to a single valve, but also enables a set of rinse equipment to be connected to the same valve, enables switching of a single valve to properly switch all equipment, and enables the metering syringe to be connected to the same valve so that it can be flushed to eliminate stale mobile phase and gas bubbles. This reduction of all functions to a single valve reduces the cost and size of instruments, and also increases reliability. While applicant has used numbers such as "1–12" to identify the stator passages, and prefers to use a valve of the type illustrated which has twelve different passages (plus the passage part 100), it should be noted that it is possible to not use some of the twelve indicated passages.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. A sample injector valve system for receiving a sample from a well and directing the sample into a sample loop that has inner and outer ends, and for injecting the sample from the loop into a chromatographic column or other analyzing device, including a stator and including an adjacent rotor that is pivotable about an axis between a plurality of rotor positions relative to said stator, where said stator has a plurality of stator passages with passage ends lying on an imaginary circle that is concentric with said axis and with opposite tube-connect ports, said loop ends and said analyzing device each being connected to a different one of said ports, and said rotor has a plurality of channels with channel ends lying on said imaginary circle, with each channel connecting a pair of said passage ends at each of said plurality of rotor portions, characterized by:

said stator has at least nine passages with a majority of passage ends spaced apart by an angle of 30° about said axis along an imaginary circle centered on said axis, and said rotor has four channels with the ends of each channel spaced apart by 30°, and with first and second of said rotor positions spaced apart by 30°;

said rotor channels being arranged so the adjacent ends of different adjacent ones of said channels are angularly spaced by 60°;

said rotor has a channel part that extends primarily radially and that has a radially outer end that lies halfway between two adjacent ones of channels and that has a radially inner end that lies substantially at said axis;

said stator has a passage part with a passage port end that lies substantially at said axis and that connects to said radially inner end of said channel part at all of said rotor positions; and including rinse syringe means for receiving low pressure rinse fluid and supplying higher pressure rinse fluid, said rinse syringe means connected to a 10th one of said ports;

a rinse reservoir for supplying low pressure rinse fluid, said rinse reservoir connected to a 9th one of said ports;

a rinse nozzle for cleaning a sample-taking probe, said rinse nozzle connected to an 11th one of said ports;

said 9th and 10th ports being spaced by 30° and one of said channels (D) connects said 9th and 10th ports in a first of said rotor positions, to allow low pressure rinse fluid to flow from said rinse reservoir to fill said rinse syringe;

said 10th and 11th ports being spaced by 30° and one of said channels (D) connects said 10th and 11th ports in a second of said rotor positions, to allow higher pressure rinse fluid to flow from said rinse reservoir to said rinse nozzle to clean the probe.

2. A sample injector valve system for receiving a sample from a well and directing the sample into a sample loop that has inner and outer ends, and for injecting the sample from the loop into a chromatographic column or other analyzing device, including a stator and including an adjacent rotor that is pivotable about an axis between a plurality of rotor positions relative to said stator, where said stator has a plurality of stator passages with passage ends lying on an imaginary circle that is concentric with said axis and with opposite tube-connect ports, and said rotor has a plurality of channels with channel ends lying on said imaginary circle, with each channel connecting a pair of said passage ends at each of said plurality of rotor portions, characterized by:

said stator has a multiplicity of passages with passage ends spaced apart about said axis along an imaginary circle centered on said axis, said rotor has a plurality of channels with the ends of each channel spaced apart, and said rotor channels are arranged with the adjacent ends of different adjacent ones of said channels being angularly spaced apart;

said rotor has a channel part that extends primarily radially and that has a radially outer end that lies halfway between two adjacent ones of channels and that has a radially inner end that lies substantially at said axis;

said stator has a passage part with a passage port end that lies substantially at said axis and that connects to said radially inner end of said channel part at all of said rotor positions.

3. A sample injector valve system for receiving a sample from a well and directing the sample into a sample loop that has inner and outer ends, and for injecting the sample from the loop into a chromatographic column or other analyzing device, including a stator and including an adjacent rotor that is pivotable about an axis between a plurality of rotor positions relative to said stator, where said stator has a plurality of stator passages with passage ends lying on an imaginary circle that is concentric with said axis and with opposite tube-connect ports, and said rotor has a plurality of channels with channel ends lying on said imaginary circle, with each channel connecting a pair of said passage ends at each of said plurality of rotor portions, characterized by:

said stator has at least nine passages with a majority of passage ends spaced apart by an angle of 30° about said axis along an imaginary circle centered on said axis, and said rotor has four channels with the ends of each channel spaced apart by 30°, and with first and second of said rotor positions spaced apart by 30°;

said rotor channels being arranged so the adjacent ends of different adjacent ones of said channels are angularly spaced by 60°;

said rotor has a channel part that extends primarily radially and that has a radially outer end that lies halfway between two adjacent ones of channels and that has a radially inner end that lies substantially at said axis;

said stator has a passage part with a passage port end that lies substantially at said axis and that connects to said radially inner end of said channel part at all of said rotor positions.

* * * * *